United States Patent
Yamada et al.

[11] Patent Number: 5,820,782
[45] Date of Patent: Oct. 13, 1998

[54] OPTICALLY ACTIVE COMPOUND AND ANTIFERROELECTRIC LIQUID CRYSTAL COMPOSITION CONTAINING THE SAME

[75] Inventors: Mamoru Yamada; Akio Yamaguchi; Shinya Yamada; Yukiharu Iwaya; Hitoshi Kondo; Toshimitsu Hagiwara, all of Kanagawa, Japan

[73] Assignee: Takasago International Corporation, Tokyo, Japan

[21] Appl. No.: 901,236

[22] Filed: Jul. 25, 1997

[30] Foreign Application Priority Data

Jul. 26, 1996 [JP] Japan .................................. 8-214045
Jun. 13, 1997 [JP] Japan .................................. 9-171247

[51] Int. Cl.$^6$ .......................... C09K 19/34; C09K 19/20; C07D 239/02
[52] U.S. Cl. ............................. 252/299.61; 252/299.67; 544/298; 544/335
[58] Field of Search ................. 252/299.01, 299.61, 252/299.67; 544/335, 298

[56] References Cited

FOREIGN PATENT DOCUMENTS

| | | |
|---|---|---|
| 0339414 | 11/1989 | European Pat. Off. . |
| 4-29954 | 1/1992 | Japan . |
| 5306247 | 11/1993 | Japan . |
| 7-10846 | 1/1995 | Japan . |

OTHER PUBLICATIONS

Moelburg et al., "Mesogenic Compounds with two Chiral Lateral Groups: New Chiral Dopants for ferroelectric Crystals", Mol. Cryst. Liq. Cryst. vol. 192 pp. 335–343, 1990.

*Primary Examiner*—Shean C. Wu
*Attorney, Agent, or Firm*—Sughrue, Mion, Zinn, Macpeak & Seas, PLLC

[57] ABSTRACT

Disclosed is a novel optically active compound which exhibits an antiferroelectric liquid crystal phase and has a low threshold voltage and a low viscosity, a novel optically active compound which doesn't exhibit an antiferroelectric liquid crystal phase but can be incorporated in an antiferroelectric liquid crystal having a high threshold voltage to reduce the threshold voltage thereof, an antiferroelectric liquid crystal composition containing the compound, and a process for the reduction of the threshold voltage of an antiferroelectric liquid crystal composition.

3 Claims, 1 Drawing Sheet

Vth (THRESHOLD VOLTAGE)=(V+V')/2

OPTICALLY ACTIVE COMPOUND AND ANTIFERROELECTRIC LIQUID CRYSTAL COMPOSITION CONTAINING THE SAME

FIELD OF THE INVENTION

The present invention relates to a novel optically active compound having a plurality of asymmetric carbon atoms useful as a liquid crystal material to be incorporated in an optical switching element employing a liquid crystal. More particularly, the present invention relates to an antiferroelectric liquid crystal composition containing such an optically active compound.

BACKGROUND OF THE INVENTION

The antiferroelectric liquid crystal was discovered by Chandani et al. in 1988 (Chandani et al., *Jpn. J. Appl. Phys.*, 27, L279 (1988).) and has been noted as a future liquid crystal substituting for the nematic liquid crystal which is incorporated in liquid crystal display devices at present.

The switching time of the nematic liquid crystal which is incorporated in liquid crystal display devices at present is as slow as typically 30 milliseconds. Thus, these display devices are fabricated such that a driving method employing a thin film transistor (TFT) requiring a very high production cost called active matrix is used. Further, a display system called twisted nematic (TN) is disadvantageous in that it essentially gives a narrow viewing angle.

On the other hand, a ferroelectric liquid crystal found by Meyer et al. in 1975 (R. B. Meyer et al., *J. Phys (France)*, 36, L69, (1975)) was expected to constitute a liquid crystal display having a high definition display because of its fast response. However, this ferroelectric liquid crystal can hardly perform gradient (gray) display and thus cannot realize full-color display yet.

The foregoing antiferroelectric liquid crystal has a switching time as fast as several tens of microseconds. In the antiferroelectric liquid crystal, liquid crystal molecules make response in plane. Thus, a wide viewing angle can be given. Further, the antiferroelectric liquid crystal exhibits a definite threshold voltage even when subjected to application of dc voltage and thus can be easily driven. Accordingly, the antiferroelectric liquid crystal can constitute a display device driven by a driving method requiring a low production cost called simple matrix. Though being made on an experimental basis, a full-color animation display has been realized.

As mentioned above, the liquid crystal display employing an antiferroelectric liquid crystal is expected to realize a high fidelity display having a wide viewing angle with a low cost simple matrix.

However, compounds exhibiting an antiferroelectric liquid crystal phase are extremely restricted from the structural point of view. The most of these compounds have a terminal structure such as 1-substituted alkylbenzoic acid ester as exemplified by the following structural formula (see *Future Liquid Crystal Display and Its materials*, supervised by Atsuo Fukuda, CMC, (1992)):

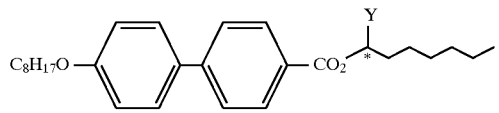

wherein Y represents an alkyl group or a perfluoroalkyl group.

The antiferroelectric liquid crystal to be incorporated in display devices must have a practical working temperature range as the nematic liquid crystal in general use and exhibit various properties concerning display quality. Thus, it is necessary that antiferroelectric liquid crystal compounds having different properties be mixed to form the desired liquid crystal composition. However, since the structure that allows the appearance of an antiferroelectric liquid crystal phase is restricted as mentioned above, allowable structural modifications are only the introduction of alicyclic group, condensed ring or heterocyclic group into the core structure and the introduction of ether bond into chiral terminal alkyl chain. The resulting compound is very akin to the original compound in properties. Thus, a practical liquid crystal composition which must have various properties can hardly be obtained. Further, it is known that a compound having a plurality of ester bonds in the molecule as mentioned above has a high viscosity and thus can hardly exhibit a fast switching time. Thus, the development of liquid crystal compounds having different properties is indispensable to obtain an antiferroelectric liquid crystal having practical properties.

On the other hand, the inventors have found that a compound having the following structure can exhibit an antiferroelectric liquid crystal phase (see JP-A-4-82862 (The term "J" as used herein means an "unexamined published Japanese patent application")).

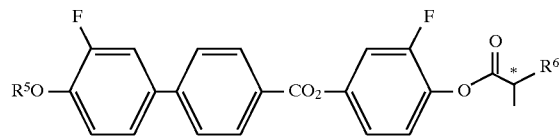

This compound has 2-methylalkanoic acid incorporated therein and thus exhibits a stable antiferroelectric liquid crystal phase. However, this compound is disadvantageous in that it exhibits a high viscosity because its core structure is similar to that of the known antiferroelectric liquid crystal and it has a high threshold voltage.

The inventors also have found that an antiferroelectric liquid crystal phase appears when 2-methylalkanoic acid is introduced into the core of a heterocyclic compound such as diphenyl pyrimidine (see JP-A-9-31063). This compound has a lower viscosity and can response faster than the foregoing ester compounds and thus is useful. However, this compound is disadvantageous in that this compound, too, has a high threshold voltage.

Under these circumstances, the inventors sought a liquid crystal compound which exhibits an antiferroelectric liquid crystal phase and exhibits a low viscosity and a low threshold voltage and an optically active compound which can reduce the threshold voltage of the foregoing antiferroelectric liquid crystal having a high threshold voltage. As a result, it was found that the introduction of a plurality of asymmetric carbon atoms provides a compound which exhibits an antiferroelectric liquid crystal phase by itself and exhibits a low threshold voltage or a compound which exhibits no antiferroelectric liquid crystal phase but can be incorporated in the foregoing compound having a high threshold voltage to lower the threshold voltage thereof. Thus, the present invention has been worked out.

SUMMARY OF THE INVENTION

An object of the present invention is to provide a novel optically active compound which exhibits an antiferroelectric liquid crystal phase and exhibits a low viscosity and a low threshold voltage, a novel optically active compound which exhibits no antiferroelectric liquid crystal phase but can be incorporated in an antiferroelectric liquid crystal having a high threshold voltage to lower the threshold voltage thereof and an antiferroelectric liquid crystal composition containing such a novel optically active compound.

The inventors made extensive studies of a novel optically active compound which exhibits an antiferroelectric liquid crystal phase and exhibits a low viscosity and a low threshold voltage, a novel optically active compound which exhibits no antiferroelectric liquid crystal phase but can be incorporated in an antiferroelectric liquid crystal having a high threshold voltage to lower the threshold voltage thereof. As a result, the present invention has been worked out.

In other words, the first aspect of the present invention relates to an optically active compound and more particularly to an optically active compound represented by the following general formula (I):

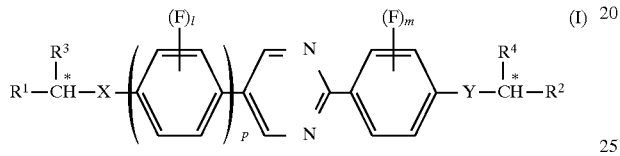

wherein $R^1$ represents an alkyl group of 5 to 10 carbon atoms; $R^2$ represents an alkyl group of 3 to 10 carbon atoms or an alkyl group of 4 to 12 carbon atoms having a $C_{1-3}$ branched group; $R^3$ represents a fluorine atom, a methyl group or a trifluoromethyl group; $R^4$ represents a methyl group, a fluorine atom or a trifluoromethyl group; l, m and p each represent 0 or 1; X represents —$(CH_2)_q$—O—, —OCO— or —$CO_2$—; Y represents —OCO—, —$CO_2$— or —O—$(CH_2)_n$— in which n and q each represent 1 or 2, with the proviso that in the case where p is 1, $R^3$ represents a fluorine atom, if X is —$(CH_2)_q$—O—, and $R^4$ represents a fluorine atom, if Y is —O—$(CH_2)_n$—, or in the case where p is 0, neither $R^3$ nor $R^4$ is a fluorine atom, if X is —$(CH_2)_q$—O— or —$CO_2$— and Y is —OCO— or —O—$(CH_2)_n$—; and C* represents an asymmetric carbon atom.

The second aspect of the present invention relates to a liquid crystal composition and more particularly to an antiferroelectric liquid crystal composition containing at least one optically active compound according to the first aspect of the present invention.

The third aspect of the present invention relates to a process and more particularly to a process for the reduction of the threshold voltage of an antiferroelectric liquid crystal composition which comprises incorporating at least one optically active compound according to the first aspect of the present invention into an antiferroelectric liquid crystal composition.

DETAILED DESCRIPTION OF THE INVENTION

Figure 1:
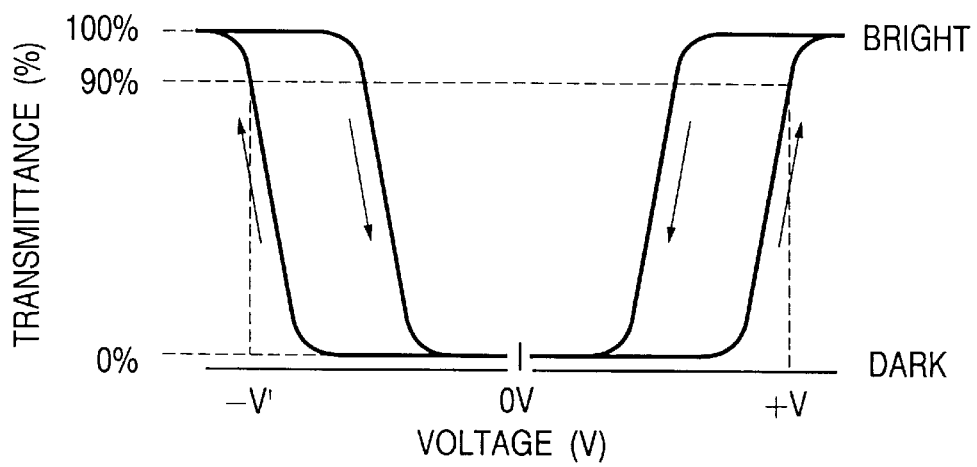
FIG. 1 illustrates an electro-optical response (double hysteresis) observed in an antiferroelectric liquid crystal and gives definition of threshold voltage.

The present invention will be further described hereinafter.

As a preferred optically active compound of the present invention there is exemplified a compound of the foregoing general formula (I) wherein $R^3$, $R^4$, X, Y, l, m, n, p and q are as defined in Tables 1 to 4 below, $R^1$, which is not set forth in these tables, is selected from the group consisting of pentyl group, hexyl group, heptyl group, octyl group, nonyl group and decyl group, and $R^2$, which is not set forth in these tables, is selected from the group consisting of propyl group, butyl group, pentyl group, hexyl group, heptyl group, octyl group, nonyl group, decyl group, $C_{4-11}$ methyl-substituted alkyl group, $C_{5-12}$ ethyl-substituted alkyl group, $C_{5-12}$ dimethyl-substituted alkyl group, $C_{6-12}$ propyl-substituted alkyl group and trimethylalkyl group.

TABLE 1

| No. | $R^3$ | p | X | q | l | m | Y | n | $R^4$ |
|---|---|---|---|---|---|---|---|---|---|
| 1 | F | 1 | —(CH₂)q-O— | 1 | 0 | 0 | —OCO— | — | CH₃ |
| 2 | F | 1 | —(CH₂)q-O— | 1 | 1(2) | 0 | —OCO— | — | CH₃ |
| 3 | F | 1 | —(CH₂)q-O— | 1 | 0 | 1(2) | —OCO— | — | CH₃ |
| 4 | F | 1 | —(CH₂)q-O— | 1 | 1(2) | 1(2) | —OCO— | — | CH₃ |
| 5 | F | 1 | —(CH₂)q-O— | 1 | 1(3) | 0 | —OCO— | — | CH₃ |
| 6 | F | 1 | —(CH₂)q-O— | 1 | 0 | 1(3) | —OCO— | — | CH₃ |
| 7 | F | 1 | —(CH₂)q-O— | 1 | 1(3) | 1(3) | —OCO— | — | CH₃ |
| 8 | F | 1 | —(CH₃)q-O— | 1 | 1(3) | 1(2) | —OCO— | — | CH₃ |
| 9 | F | 1 | —(CH₂)q-O— | 1 | 1(2) | 1(3) | —OCO— | — | CH₃ |
| 10 | F | 1 | —(CH₂)q-O— | 2 | 0 | 0 | —OCO— | — | CH₃ |
| 11 | F | 1 | —(CH₂)q-O— | 2 | 1(2) | 0 | —OCO— | — | CH₃ |
| 12 | F | 1 | —(CH₂)q-O— | 2 | 0 | 1(2) | —OCO— | — | CH₃ |
| 13 | F | 1 | —(CH₂)q-O— | 2 | 1(2) | 1(2) | —OCO— | — | CH₃ |
| 14 | F | 1 | —(CH₂)q-O— | 2 | 1(3) | 0 | —OCO— | — | CH₃ |
| 15 | F | 1 | —(CH₂)q-O— | 2 | 0 | 1(3) | —OCO— | — | CH₃ |
| 16 | F | 1 | —(CH₂)q-O— | 2 | 1(3) | 1(3) | —OCO— | — | CH₃ |
| 17 | F | 1 | —(CH₂)q-O— | 2 | 1(3) | 1(2) | —OCO— | — | CH₃ |
| 18 | F | 1 | —(CH₂)q-O— | 2 | 1(2) | 1(3) | —OCO— | — | CH₃ |
| 19 | F | 0 | —(CH₂)q-O— | 1 | — | 0 | —OCO— | — | CH₃ |
| 20 | F | 0 | —(CH₂)q-O— | 1 | — | 1(2) | —OCO— | — | CH₃ |
| 21 | F | 0 | —(CH₂)q-O— | 1 | — | 1(3) | —OCO— | — | CH₃ |
| 22 | F | 0 | —(CH₂)q-O— | 2 | — | 0 | —OCO— | — | CH₃ |
| 23 | F | 0 | —(CH₂)q-O— | 2 | — | 1(2) | —OCO— | — | CH₃ |
| 24 | F | 0 | —(CH₂)q-O— | 2 | — | 1(3) | —OCO— | — | CH₃ |
| 25 | CF₃ | 1 | —OCO— | — | 0 | 0 | —O—(CH₂)n— | 1 | F |
| 26 | CF₃ | 1 | —OCO— | — | 0 | 1(3) | —O—(CH₂)n— | 1 | F |

TABLE 1-continued

| No. | R³ | p | X | q | l | m | Y | n | R⁴ |
|---|---|---|---|---|---|---|---|---|---|
| 27 | CF₃ | 1 | —OCO— | — | 1(3) | 0 | —O—(CH₂)n— | 1 | F |
| 28 | CF₃ | 1 | —OCO— | — | 1(3) | 1(3) | —O—(CH₂)n— | 1 | F |

TABLE 2

| No. | R³ | p | X | q | l | m | Y | n | R⁴ |
|---|---|---|---|---|---|---|---|---|---|
| 29 | CF₃ | 1 | —OCO— | — | 1(2) | 0 | —O—(CH₂)n— | 1 | F |
| 30 | CF₃ | 1 | —OCO— | — | 0 | 1(2) | —O—(CH₂)n— | 1 | F |
| 31 | CF₃ | 1 | —OCO— | — | 1(2) | 1(2) | —O—(CH₂)n— | 1 | F |
| 32 | CF₃ | 1 | —OCO— | — | 1(2) | 1(3) | —O—(CH₂)n— | 1 | F |
| 33 | CF₃ | 1 | —OCO— | — | 1(3) | 1(2) | —O—(CH₂)n— | 1 | F |
| 34 | CF₃ | 1 | —OCO— | — | 0 | 0 | —O—(CH₂)n— | 2 | F |
| 35 | CF₃ | 1 | —OCO— | — | 0 | 1(3) | —O—(CH₂)n— | 2 | F |
| 36 | CF₃ | 1 | —OCO— | — | 1(3) | 0 | —O—(CH₂)n— | 2 | F |
| 37 | CF₃ | 1 | —OCO— | — | 1(3) | 1(3) | —O—(CH₂)n— | 2 | F |
| 38 | CF₃ | 1 | —OCO— | — | 1(2) | 0 | —O—(CH₂)n— | 2 | F |
| 39 | CF₃ | 1 | —OCO— | — | 0 | 1(2) | —O—(CH₂)n— | 2 | F |
| 40 | CF₃ | 1 | —OCO— | — | 1(2) | 1(2) | —O—(CH₂)n— | 2 | F |
| 41 | CF₃ | 1 | —OCO— | — | 1(2) | 1(3) | —O—(CH₂)n— | 2 | F |
| 42 | CF₃ | 1 | —OCO— | — | 1(3) | 1(2) | —O—(CH₂)n— | 2 | F |
| 43 | F | 1 | —(CH₂)q-O— | 1 | 0 | 1 | —CO₂— | — | CF₃ |
| 44 | F | 1 | —(CH₂)q-O— | 1 | 1(3) | 1 | —CO₂— | — | CF₃ |
| 45 | F | 1 | —(CH₂)q-O— | 1 | 0 | 1(3) | —CO₂— | — | CF₃ |
| 46 | F | 1 | —(CH₂)q-O— | 1 | 1(3) | 1(3) | —CO₂— | — | CF₃ |
| 47 | F | 1 | —(CH₂)q-O— | 1 | 1(2) | 0 | —CO₂— | — | CF₃ |
| 48 | F | 1 | —(CH₂)q-O— | 1 | 0 | 1(2) | —CO₂— | — | CF₃ |
| 49 | F | 1 | —(CH₂)q-O— | 1 | 1(2) | 1(2) | —CO₃— | — | CF₃ |
| 50 | F | 1 | —(CH₂)q-O— | 1 | 1(2) | 1(3) | —CO₂— | — | CF₃ |
| 51 | F | 1 | —(CH₂)q-O— | 1 | 1(3) | 1(2) | —CO₂— | — | CF₃ |
| 52 | CF₃ | 1 | —OCO— | — | 0 | 0 | —OCO— | — | CH₃ |
| 53 | CF₃ | 1 | —OCO— | 1 | 1(3) | 0 | —OCO— | — | CH₃ |
| 54 | CF₃ | 1 | —OCO— | 1 | 0 | 1(3) | —OCO— | — | CH₃ |

TABLE 3

| No. | R³ | p | X | q | l | m | Y | n | R⁴ |
|---|---|---|---|---|---|---|---|---|---|
| 55 | CF₃ | 1 | —OCO— | 1 | 1(3) | 1(3) | —OCO— | — | CH₃ |
| 56 | CF₃ | 1 | —OCO— | 1 | 1(2) | 0 | —OCO— | — | CH₃ |
| 57 | CF₃ | 1 | —OCO— | 1 | 0 | 1(2) | —OCO— | — | CH₃ |
| 58 | CF₃ | 1 | —OCO— | 1 | 1(2) | 1(2) | —OCO— | — | CH₃ |
| 59 | CF₃ | 1 | —OCO— | 1 | 1(2) | 1(3) | —OCO— | — | CH₃ |
| 60 | CF₃ | 1 | —OCO— | 1 | 1(3) | 1(2) | —OCO— | — | CH₃ |
| 61 | F | 1 | —(CH₂)q-O— | 1 | 0 | 0 | —O—(CH₂)n— | 1 | F |
| 62 | F | 1 | —(CH₂)q-O— | 1 | 1(3) | 0 | —O—(CH₂)n— | 1 | F |
| 63 | F | 1 | —(CH₂)q-O— | 1 | 0 | 1(3) | —O—(CH₂)n— | 1 | F |
| 64 | F | 1 | —(CH₂)q-O— | 1 | 1(3) | 1(3) | —O—(CH₂)n— | 1 | F |
| 65 | F | 1 | —(CH₂)q-O— | 1 | 1(2) | 0 | —O—(CH₂)n— | 1 | F |
| 66 | F | 1 | —(CH₂)q-O— | 1 | 0 | 1(2) | —O—(CH₂)n— | 1 | F |
| 67 | F | 1 | —(CH₂)q-O— | 1 | 1(2) | 1(2) | —O—(CH₂)n— | 1 | F |
| 68 | F | 1 | —(CH₂)q-O— | 1 | 1(2) | 1(3) | —O—(CH₂)n— | 1 | F |
| 69 | F | 1 | —(CH₂)q-O— | 1 | 1(3) | 1(2) | —O—(CH₂)n— | 1 | F |
| 70 | F | 1 | —(CH₂)q-O— | 1 | 0 | 0 | —O—(CH₂)n— | 2 | F |
| 71 | F | 1 | —(CH₂)q-O— | 1 | 1(3) | 0 | —O—(CH₂)n— | 2 | F |
| 72 | F | 1 | —(CH₂)q-O— | 1 | 0 | 1(3) | —O—(CH₂)n— | 2 | F |
| 73 | F | 1 | —(CH₂)q-O— | 1 | 1(3) | 1(3) | —O—(CH₂)n— | 2 | F |
| 74 | F | 1 | —(CH₂)q-O— | 1 | 1(2) | 0 | —O—(CH₂)n— | 2 | F |
| 75 | F | 1 | —(CH₂)q-O— | 1 | 0 | 1(2) | —O—(CH₂)n— | 2 | F |
| 76 | F | 1 | —(CH₂)q-O— | 1 | 1(2) | 1(2) | —O—(CH₂)n— | 2 | F |
| 77 | F | 1 | —(CH₂)q-O— | 1 | 1(2) | 1(3) | —O—(CH₂)n— | 2 | F |
| 78 | F | 1 | —(CH₂)q-O— | 1 | 1(3) | 1(2) | —O—(CH₂)n— | 2 | F |
| 79 | F | 1 | —(CH₂)q-O— | 2 | 0 | 0 | —O—(CH₂)n— | 1 | F |
| 80 | F | 1 | —(CH₂)q-O— | 2 | 1(3) | 0 | —O—(CH₂)n— | 1 | F |

TABLE 4

| No. | R³ | p | X | q | l | m | Y | n | R⁴ |
|---|---|---|---|---|---|---|---|---|---|
| 81 | F | 1 | —(CH₂)q-O— | 2 | 0 | 1(3) | —O—(CH₂)n— | 1 | F |
| 82 | F | 1 | —(CH₂)q-O— | 2 | 1(3) | 1(3) | —O—(CH₂)n— | 1 | F |
| 83 | F | 1 | —(CH₂)q-O— | 2 | 1(2) | 0 | —O—(CH₂)n— | 1 | F |
| 84 | F | 1 | —(CH₂)q-O— | 2 | 0 | 1(2) | —O—(CH₂)n— | 1 | F |

TABLE 4-continued

| No. | $R^3$ | p | X | q | l | m | Y | n | $R^4$ |
|---|---|---|---|---|---|---|---|---|---|
| 85 | F | 1 | —(CH$_2$)q-O— | 2 | 1(2) | 1(2) | —O—(CH$_2$)n— | 1 | F |
| 86 | F | 1 | —(CH$_2$)q-O— | 2 | 1(2) | 1(3) | —O—(CH$_2$)n— | 1 | F |
| 87 | F | 1 | —(CH$_2$)q-O— | 2 | 1(3) | 1(2) | —O—(CH$_2$)n— | 1 | F |
| 88 | F | 1 | —(CH$_2$)q-O— | 2 | 0 | 0 | —O—(CH$_2$)n— | 2 | F |
| 89 | F | 1 | —(CH$_2$)q-O— | 2 | 1(3) | 0 | —O—(CH$_2$)n— | 2 | F |
| 90 | F | 1 | —(CH$_2$)q-O— | 2 | 0 | 1(3) | —O—(CH$_2$)n— | 2 | F |
| 91 | F | 1 | —(CH$_2$)q-O— | 2 | 1(3) | 1(3) | —O—(CH$_2$)n— | 2 | F |
| 92 | F | 1 | —(CH$_2$)q-O— | 2 | 1(2) | 0 | —O—(CH$_2$)n— | 2 | F |
| 93 | F | 1 | —(CH$_2$)q-O— | 2 | 0 | 1(2) | —O—(CH$_2$)n— | 2 | F |
| 94 | F | 1 | —(CH$_2$)q-O— | 2 | 1(2) | 1(2) | —O—(CH$_2$)n— | 2 | F |
| 95 | F | 1 | —(CH$_2$)q-O— | 2 | 1(2) | 1(3) | —O—(CH$_2$)n— | 2 | F |
| 96 | F | 1 | —(CH$_2$)q-O— | 2 | 1(3) | 1(2) | —O—(CH$_2$)n— | 2 | F |
| 97 | F | 1 | —CO$_2$— | — | 0 | 0 | —OCO— | — | CH$_3$ |
| 98 | F | 1 | —CO$_2$— | — | 1(3) | 0 | —OCO— | — | CH$_3$ |
| 99 | F | 1 | —CO$_2$— | — | 0 | 1(3) | —OCO— | — | CH$_3$ |
| 100 | F | 1 | —CO$_2$— | — | 1(3) | 1(3) | —OCO— | — | CH$_3$ |
| 101 | F | 1 | —CO$_2$— | — | 1(2) | 0 | —OCO— | — | CH$_3$ |
| 102 | F | 1 | —CO$_2$— | — | 0 | 1(2) | —OCO— | — | CH$_3$ |
| 103 | F | 1 | —CO$_2$— | — | 1(2) | 1(2) | —OCO— | — | CH$_3$ |
| 104 | F | 1 | —CO$_2$— | — | 1(2) | 1(3) | —OCO— | — | CH$_3$ |
| 105 | F | 1 | —CO$_2$— | — | 1(3) | 1(2) | —OCO— | — | CH$_3$ |

The figure in parentheses in the column of l and m in the above tables indicates substitution site.

Some of the various compounds of the present invention having the specified basic structure set forth in the tables above exhibit an antiferroelectric liquid crystal phase by themselves and exhibit a low threshold voltage in the antiferroelectric liquid crystal phase. The other compounds don't exhibit an antiferroelectric liquid crystal phase but can be incorporated in an antiferroelectric liquid crystal having a high threshold voltage to lower the threshold voltage thereof. Further, two or more of the various compounds of the present invention may be used in admixture.

Moreover, the compound of the present invention has a good miscibility with a known antiferroelectric liquid crystal compound and thus can easily form an antiferroelectric liquid crystal composition also when mixed therewith. As a preferred example of such a known antiferroelectric liquid crystal compound there may be used a compound terminated by the following groups:

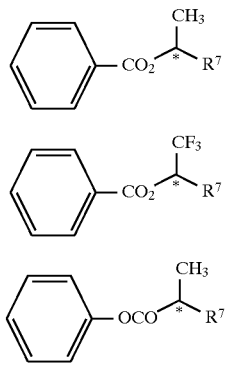

wherein $R^7$ represents a straight-chain alkyl group or an alkyl group having an ether bond.

Particularly preferred examples of such a compound will be given below.

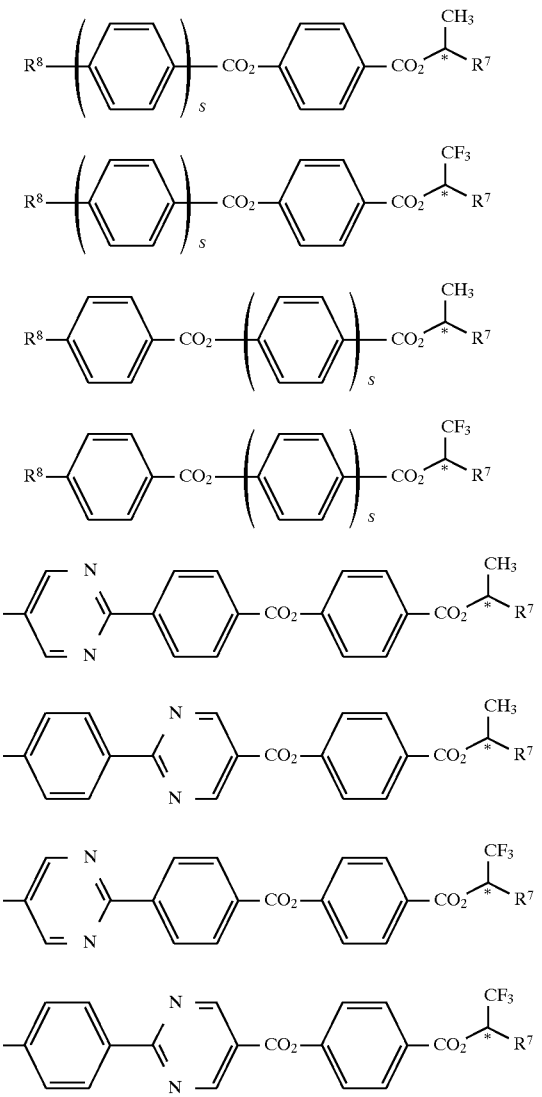

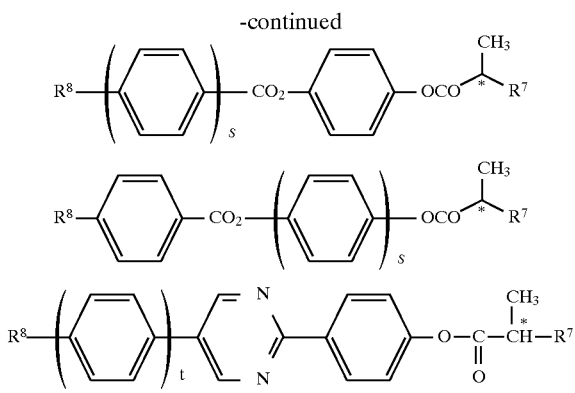

wherein R⁷ represents a straight-chain alkyl group or an alkyl group having an ether bond; R⁸ represents an alkyl group or an alkoxy group; s represents 1 or 2; and t represents 0 or 1.

Other examples of the foregoing compound include compounds obtained by substituting some of hydrogen atoms in the phenylene group in the foregoing general formulae by fluorine atoms.

In the case where the optically active compounds of the present invention and the foregoing known antiferroelectric liquid crystal compounds or their compositions are mixed to obtain an antiferroelectric liquid crystal composition, the content of compounds showing an antiferroelectric liquid crystal phase among the optically active compounds of the present invention is preferably from 1 to 80% by weight. However, among the optically active compounds of the present invention represented by the general formula (I), the content of the compound wherein p is 0 exhibits a low upper limit temperature for antiferroelectric liquid crystal phase and thus lowers the upper limit temperature of the composition which can exhibit an antiferroelectric liquid crystal phase. Therefore, such an optically active compound is preferably incorporated in an amount of from 1 to 50% by weight.

Among the optically active compounds of the present invention, those which don't exhibit an antiferroelectric liquid crystal phase or liquid crystal phase can be incorporated in an antiferroelectric liquid crystal compound or its composition having a high threshold voltage in an amount from 1 to 30% by weight to exhibit a stable antiferroelectric liquid crystal phase and lower the threshold voltage thereof. Therefore, even a compound which doesn't exhibit an antiferroelectric liquid crystal phase or liquid phase is preferably incorporated in an amount of from 1 to 30% by weight.

On the other hand, the optically active compound of the present invention has a good miscibility with a known compound which exhibits a smectic C phase or chiral smectic C phase but doesn't exhibit an antiferroelectric liquid crystal phase, such as phenylpyrimidine and phenyl benzoate. Therefore, the optically active compound of the present invention can be mixed with such a compound so far as the layer structure of antiferroelectric liquid crystal phase can be maintained to obtain a desired antiferroelectric liquid crystal composition. In this case, the content of the compound which exhibits a smectic C phase or chiral smectic C phase but doesn't exhibit an antiferroelectric liquid crystal phase is preferably not more than 40% by weight, more preferably not more than 30% by weight.

Thus, most of the liquid crystal compounds of the present invention stably exhibit an antiferroelectric liquid crystal phase and can be incorporated in electro-optic elements and other like elements employing an antiferroelectric liquid crystal. Further, the compound of the present invention has a good miscibility with many known conventional liquid crystal compounds and thus can provide a liquid crystal material having improved temperature characteristics.

Further, the optically active compound of the present invention can be incorporated in an antiferroelectric liquid crystal compound having a high threshold voltage to lower the threshold voltage thereof, making it possible to obtain an even more desirable antiferroelectric liquid crystal composition.

The optically active compound of the present invention represented by the foregoing general formula (I) can be synthesized by, e.g., the following method. For example, optically active 2-methylalkanoic acids can be obtained by asymmetrically hydrogenating the corresponding 2-methyl-2-alkenoic acid or by optically resolving the racemic modification of 2-methylalkanoic acid or derivative thereof with lipase or the like.

Further, an optically active 2- or 3-fluoroalkyl derivative can be synthesized by fluorinating the corresponding 2- or 3-hydroxyalkyl derivative with a fluorinating agent such as hexafluoropropene diethylamine.

Moreover, 2-fluoroalkanoic acids can be obtained by asymmetrically hydrogenating 2-fluoro-2-alkenoic acid. 2-Fluoroalkyl derivatives can be obtained by a process which comprises reducing 2-fluoroalkanoic acids to 2-fluoroalkanol which is then reacted with mesyl chloride or tosyl chloride in the presence of a base such as pyridine to produce a desired derivative. 1,1,1-Trifluoro-2-alkanols can be obtained by, e.g., the optical resolution of the corresponding compounds with lipase.

The core moiety of the compound of the present invention can be synthesized by any ordinary method. The protective group to be positioned at both ends of the core moiety is then selected. The core moiety and the protective group are then sequentially reacted with the corresponding optically active compounds to obtain the compound of the present invention.

A method for the synthesis of the compound of the general formula (I) wherein p is 1, X is —(CH₂)_q—O— and Y is —OCO— will be described hereinafter. Firstly, a diphenylpyrimidine derivative is obtained from a perchlorate derivative of (3-dimethylamino-2-phenylpropenylidene) dimethyl ammonium having a protective group such as benzyl group incorporated therein and a p-hydroxybenzamidinehydrochloric acid salt by an ordinary method. The free hydroxyl group is then protected by 3,4-dihydro-2H-pyrane, vinyl ethyl ether, p-methoxybenzyl chloride or the like (R¹⁰) while the other protective group is released (R⁹: If the other protective group is a benzyl group, it is released by palladium-carbon). Thereafter, the derivative is etherified with 2-fluoroalkyl mesylate, 2-fluoroalkyl tosylate or the like. The other protective group is then eliminated by an acid or the like. The derivative thus etherified is then subjected to ordinary esterification to obtain the desired compound. An example of the synthesis route will be given below.

(1)=1, X=—(CH₂)_q—O—, Y=—OCO—

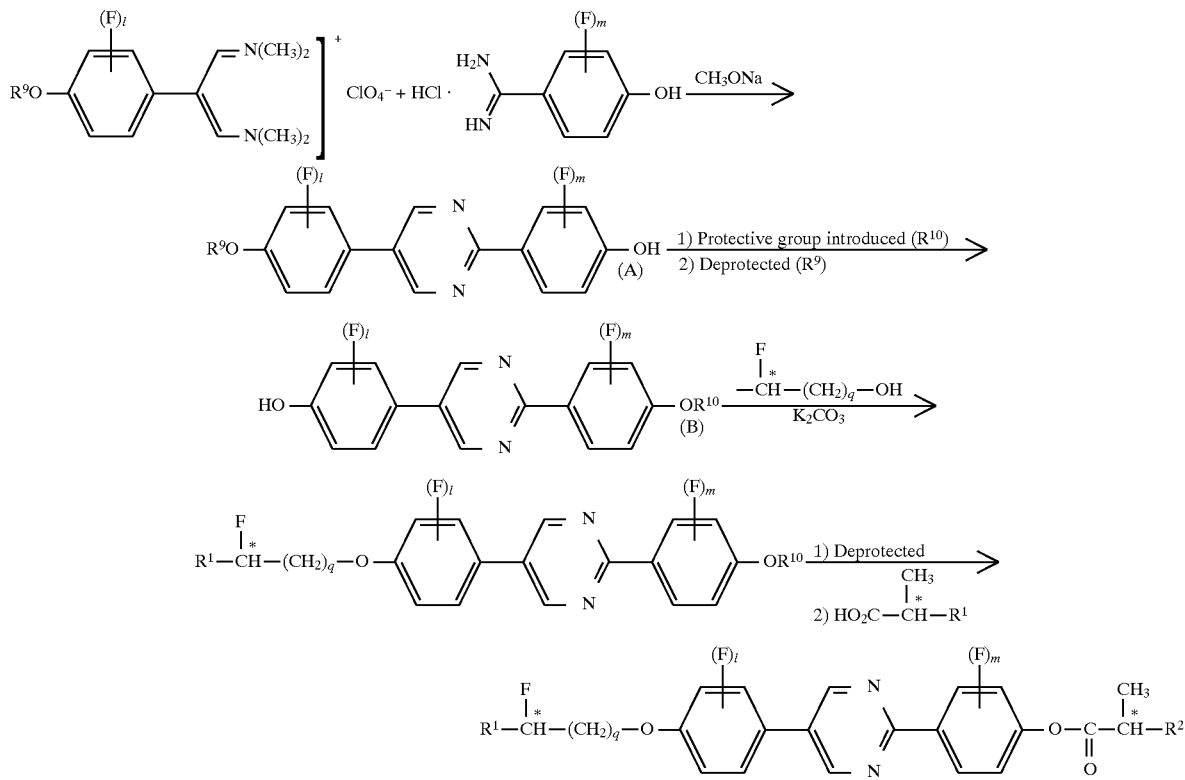

A method for the synthesis of the compound of the general formula (I) wherein p is 0, X is —(CH$_2$)$_q$—O— and Y is —OCO— will be described hereinafter. It goes without saying that this compound can be synthesized by the foregoing pyrimidine ring formation method. This time, however, a synthesis method by cross coupling reaction of 2-chloro-5-methoxy-1,3-pyrimidine with a Grignard reagent prepared from a phenyl halide having substituents in the presence of a nickel catalyst was employed. The methoxy compound thus obtained is then heated in the presence of sodium hydroxide to undergo demethylation. The compound thus demethylated is then subjected to etherification, deprotection and esterification in the same manner as in the foregoing reaction to synthesize the desired compound. The scheme of the synthesis route will be given below.

(2) p=0, X=—(CH$_2$)$_q$—O—, Y=—OCO—

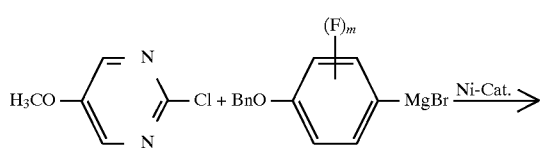

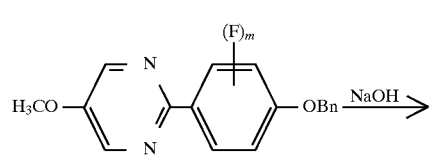

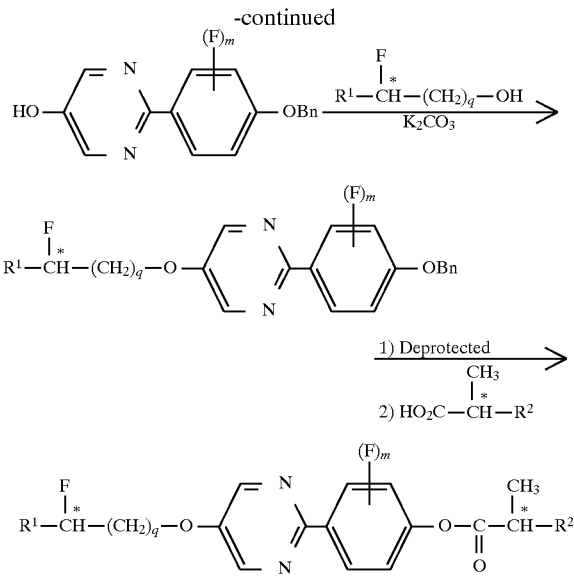

(3) The compound of the general formula (I) wherein X is —CO$_2$— and Y is —OCO— or —O—(CH$_2$)$_n$— can be obtained by reacting the foregoing compound (A) with 2-substituted alkanoic acid, 2-fluoroalkyl mesylate or the like, eliminating the other protective group from the compound with an acid or the like, and then subjecting the compound to ordinary esterification to obtain the desired compound.

(4) The compound of the general formula (I) wherein X is —OCO— or Y is —CO$_2$— can be similarly synthesized from the following compound:

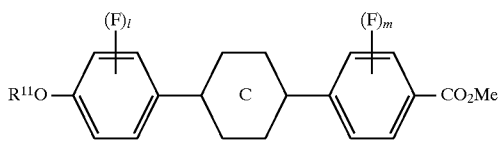

wherein the ring C represents 1,3-pyrimidine ring; and R" represents a protective group such as benzyl group.

(5) The compound of the general formula (I) wherein X is —$(CH_2)_qO$— and Y is —$O(CH_2)_n$— can be synthesized by deprotecting the compound (A) set forth in the foregoing synthesis route, and then etherifying the compound with a two-fold molar amount of 2-fluoroalkyl mesylate or the like.

EXAMPLES

The present invention will be further described in the following examples, but the present invention should not be construed as being limited thereto. The phase transition point as used hereinafter was determined by visual observation under a polarizing microscope equipped with a hot stage and measurement by a differential scanning calorimeter (DSC). The judgement of various liquid crystal phases was carried out by so-called miscibility test and contact method.

For the evaluation of various liquid crystal compounds and compositions, a liquid crystal evaluation cell was employed obtained by providing a transparent conductive layer (indium tin oxide: ITO) on two sheets of glass substrates, coating these glass substrates with an oriented film made of a polyimide, polyvinyl alcohol or the like, rubbing these glass substrates, and then laminating these glass substrates in such an arrangement that the direction of rubbing on them are parallel to each other. The cell thus prepared had a gap of 2.3 μm.

For the measurement of electro-optical effects such as threshold voltage, a temperature-controlled liquid crystal cell disposed between a polarizer and an analyzer arranged in crossed Nicols was irradiated with He—Ne laser. Under these conditions, the response of the liquid crystal to a voltage applied was determined by observing the change of transmittance measured by a photo-electron multiplier. The threshold voltage is defined as voltage required to give a transmittance of 90% assuming that dark level corresponds to a transmittance of 0% and bright level corresponds to a transmittance of 100% under the application of triangular wave. The term "Tc" as used hereinafter is meant to indicate the upper limit temperature for antiferroelectric liquid crystal phase.

Example 1

Synthesis of 5-(4-((S)-2-fluorooctyloxy)phenyl)-2-(4-((S)-2,6-dimethylheptanoyloxy)phenyl)-1,3-pyrimidine (1) Synthesis of 5-(4-((S)-2-fluorooctyloxy)phenyl)-2-(4-(tetrahydropyranyloxyoxy)phenyl)-1,3-pyrimidine Into a reaction flask were charged 1.3 g of (S)-2-fluorooctyl tosylate, 1.25 g of 5-(4-hydroxyphenyl)-2-(4-(tetrahydropyranyloxy)phenyl)-1,3-pyrimidine, 0.67 g of potassium carbonate and 38 ml of dimethylformamide in a stream of nitrogen. The mixture was then stirred at a temperature of 80° C. in a stream of nitrogen overnight. The reaction product was allowed to cool, poured into ice water, and then extracted with ethyl acetate. The resulting organic phase was then subjected to distillation of solvent to obtain a crude reaction product. The crude reaction product was then purified through silica gel column chromatography (a 3/1 (hereinafter by volume) mixture of toluene and ethyl acetate) to obtain 1.61 g of the desired compound (yield: 94.1%).

(2) Synthesis of 5-(4-((S)-2-fluorooctyloxy)phenyl)-2-(4-hydroxyphenyl)-1,3-pyrimidine Into a reaction flask were charged 1.61 g of 5-(4-((S)-2-fluorooctyloxy)phenyl)-2-(4-(tetrahydropyranyloxy)phenyl)-1,3-pyrimidine, 30 ml of chloroform and 100 ml of methanol. To the mixture was then added 0.11 g of paratoluenesulfonic acid monohydrate at room temperature with stirring. The mixture was directly stirred at room temperature overnight. After stirring, the reaction solution was neutralized with saturated aqueous solution of sodium bicarbonate. The solvent was then distilled off the reaction solution to obtain a crude reaction product. The crude reaction product was then purified through silica gel column chromatography (toluene/ethyl acetate=1/1) to obtain 1.33 g of the desired compound (yield: 99.6%).

(3) Synthesis of 5-(4-((S)-2-fluorooctyloxy)phenyl)-2-(4-((S)-2,6-dimethylheptanoyloxy)phenyl)-1,3-pyrimidine Into a reaction flask were charged 1.33 g of 5-(4-((S)-2-fluorooctyloxy)phenyl)-2-(4-(hydroxyphenyl)-1,3-pyrimidine, 0.54 g of (S)-2,6-dimethylheptanoic acid, 20 ml of methylene chloride, 0.83 g of N,N'-dicyclohexyl carbodiimide (DCC) and a small amount of N,N-dimethylaminopyridine (DMAP). The mixture was stirred at room temperature overnight. The insoluble matter was removed by filtration. The solvent was distilled off the filtrate to obtain a crude reaction product which was then purified through silica gel column chromatography (toluene/ethyl acetate=10/1) to obtain 1.19 g of the desired compound (yield: 66.4%).

$^1$H-NMR(CDCl$_3$) δ ppm: 0.88–0.92 (m, 9H), 1.26–1.44 (m, 16H), 1.55–1.60 (m, 1H), 1.80 (m, 3H), 2.71–2.73 (m, 1H), 4.10–4.11 (m, 1H), 4.16–4.18 (m, 1H), 4.86 (dm, 1H, J=48.7 Hz), 7.08 (d, 2H, J=8.9 Hz), 7.22 (d, 2H, J=8.8 Hz), 7.57 (d, 2H, J=8.9 Hz), 8.51 (d, 2H, J=9.0 Hz), 8.97 (s, 2H)

MS(m/z): 534 (M$^+$)

This compound melted and changed to an isotropic phase at a temperature of 136.1° C. When cooled, this compound monotropically exhibited an antiferroelectric liquid crystal phase. The phase transition temperature from the antiferroelectric liquid crystal phase to the isotropic liquid was 135° C.

This compound was injected into a liquid crystal cell, and then measured for threshold voltage at a temperature of 120° C. (Tc-15° C.). As a result, the threshold voltage was 20 V. This compound exhibited an antiferroelectric liquid crystal phase directly from an isotropic phase. In general, it is difficult to orient a compound having such a phase sequence in a rubbing cell. It was found that this compound is also advantageous in that it can be fairly oriented in the foregoing liquid crystal cell.

Comparative Example 1

A compound having an optically active 2,6-dimethylheptanoic acid alone incorporated therein, i.e., 5-(4-decylphenyl)-2-(4-((S)-2,6-dimethylheptanoyloxy)phenyl)-1,3-pyrimidine was synthesized. This compound melted and exhibited an antiferroelectric liquid crystal phase at a temperature of 100.7° C. and became an isotropic phase at a temperature of 131.7° C. This compound was injected into a liquid crystal cell, and then measured for threshold voltage at a temperature of 116.7° C. (Tc-15° C.). As a result, the threshold voltage was 59 V, which is very high as compared with that of the liquid crystal of Example 1.

The compound of the present invention comprises an optically active compound fluorine-substituted alkyl group incorporated therein in addition to 2-methylalkanoic acid. This shows that the incorporation of such an optically active compound provides a remarkably improved threshold voltage.

Example 2

To the compound shown in Comparative Example 1 was added 11.1% by weight of the compound set forth in Table 1 to obtain an antiferroelectric liquid crystal composition (Tc=125° C.). This compound was injected into a liquid crystal cell, and then measured for threshold voltage at a temperature of 120° C. (Tc-5° C.). As a result, the threshold voltage was 36 V. The compound of Comparative Example 1 has a threshold voltage of 44 V at a temperature of (Tc-5° C.). Thus, it was found that the incorporation of the compound of Example 1 provides an improvement in threshold voltage, making it possible to obtain an antiferroelectric liquid crystal composition having better properties.

Example 3

Synthesis of 5-(3-fluoro-4-((S)-2-fluorooctyloxy) phenyl)-2-(3-fluoro-4-((S)-2,6-dimethylheptanoyloxy)phenyl)-1,3-pyrimidine The procedure of Example 1 was followed except that 5-(4-hydroxyphenyl)-2-(4-(tetrahydropyranyloxy)phenyl)-1,3-pyrimidine was replaced by 5-(3-fluoro-4-hydroxyphenyl)-2-(3-fluoro-4-(tetrahydropyranyloxy) phenyl)-1,3-pyrimidine in the step (1). Thus, the desired compound was obtained.

$^1$H-NMR(CDCl$_3$) δ ppm: 0.89–0.91 (m, 9H), 1.26 (m, 2H), 1.32–1.44 (m, 14H), 1.55–1.60 (m, 1H), 1.81–1.87 (m, 3H), 2.75–2.80 (m, 1H), 4.18–4.20 (m, 1H), 4.23–4.26 (m, 1H), 4.88 (dm, 1H, J=49.0 Hz), 7.12–7.16 (m, 1H), 7.22–7.24 (m, 1H), 7.33–7.40 (m, 2H), 8.28–8.33 (m, 2H), 8.97 (s, 2H)

MS(m/z): 570 (M$^+$)

This compound melted and exhibited an antiferroelectric liquid crystal phase at a temperature of 78.7° C. and changed to an isotropic phase at a temperature of 99.2° C.

Example 4

Synthesis of 5-(4-((S)-2-fluorooctyloxy) phenyl)-2-(3-fluoro-4-((S)-2-methyloctanoyloxy)phenyl)-1,3-pyrimidine The procedure of Example 1 was followed except that 5-(4-hydroxyphenyl)-2-(4-(tetrahydropyranyloxy)phenyl)-1,3-pyrimidine was replaced by 5-(4-hydroxyphenyl)-2-(3-fluoro-4-(1-ethoxyethyl)phenyl)-1,3-pyrimidine in the step (1) and (S)-2,6-dimethylheptanoic acid was replaced by (S)-2-methyloctanoic acid in the step (3). Thus, the desired compound was obtained.

$^1$H-NMR(CDCl$_3$) δ ppm: 0.89–0.94 (m, 6H), 1.31–1.48 (m, 19H), 1.55–1.60 (m, 1H), 1.81–1.86 (m, 3H), 2.76–2.81 (m, 1H), 4.10–4.21 (m, 2H), 4.88 (dm, 1H, J=48.5 Hz), 7.10 (d, 2H, J=8.8 Hz), 7.24–7.26 (m, 1H), 7.59 (d, 2H, J=8.8 Hz), 8.30–8.35 (m, 2H), 8.99 (s, 2H)

MS(m/z): 552 (M$^+$)

This compound melted and exhibited an antiferroelectric liquid crystal phase at a temperature of 98° C., changed to a ferroelectric phase at a temperature of 128° C., exhibited a smectic A phase at a temperature of 129° C. and then changed to an isotropic phase at a temperature of 142° C.

Example 5

Synthesis of 5-(3-fluoro-4-((S)-2-fluorodecyloxy) phenyl)-2-(2-fluoro-4-((S)-2,6-dimethylheptanoyloxy)phenyl)-1,3-pyrimidine (1) Synthesis of 5-(3-fluoro-4-((S)-2-fluorodecyloxy) phenyl)-2-(2-fluoro-4-(4-methoxybenzyloxy)-1,3-pyrimidine Into a reaction flask were charged 0.7 g of (S)-2-fluorodecyl tosylate, 0.9 g of 5-(4-hydroxyphenyl)-2-(2-fluoro-4-(4-methoxybenzyloxy)-1,3-pyrimidine, 0.44 g of potassium carbonate and 30 ml of DMF in a stream of nitrogen. The mixture was then stirred at a temperature of 80° C. in a stream of nitrogen overnight. The reaction product was allowed to cool, poured into ice water, and then extracted with chloroform. The resulting organic phase was then subjected to distillation of solvent to obtain 1.3 g of a crude reaction product. The crude reaction product was then purified through silica gel column chromatography (2/1 mixture of toluene and ethyl acetate) to obtain 1.1 g of the desired compound.

(2) Synthesis of 5-(3-fluoro-4-((S)-2-fluorodecyloxy) phenyl)-2-(2-fluoro-4-hydroxyphenyl)-1,3-pyrimidine Into a reaction flask were charged 1.1 g of 5-(3-fluoro-4-((S)-2-fluorodecyloxy)phenyl)-2-(2-fluoro-4-(4-methoxybenzyloxyphenyl)-1,3-pyrimidine and 50 ml of methylene chloride, to the mixture was then added dropwise 13 g of trifluoroacetic acid at room temperature. The mixture was stirred for 2 hours. After stirring, the reaction product was poured into ice water, and then extracted with chloroform. The solvent was distilled off the extract to obtain a crude reaction product which was then purified through silica gel column chromatography (toluene/ethyl acetate=5/1) to obtain 0.8 g of the desired compound.

(3) Synthesis of 5-(3-fluoro-4-((S)-2-fluorodecyloxy) phenyl)-2-(2-fluoro-4-((S)-2,6-dimethylheptanoyloxy)phenyl)-1,3-pyrimidine Into a reaction flask were charged 0.8 g of 5-(3-fluoro-4-((S)-2-fluorodecyloxy)phenyl)-2-(2-fluoro-4-hydroxyphenyl)-1,3-pyrimidine, 0.32 g of (S)-2,6-dimethylheptanoic acid, 24 ml of methylene chloride, 0.65 g of DCC and a small amount of DMAP. The mixture was stirred at room temperature overnight. The insoluble matter was removed by filtration. The solvent was distilled off the filtrate to obtain a crude reaction product which was then purified through silica gel column chromatography (toluene/ethyl acetate=3/1) to obtain 1.4 g of the desired compound.

$^1$H-NMR(CDCl$_3$) δ ppm: 0.87 (m, 9H), 1.25–1.44 (m, 20H), 1.56 (m, 1H), 1.79–1.81 (m, 3H), 2.71–2.72 (m, 1H), 4.18–4.21 (m, 1H), 4.24–4.26 (m, 1H), 4.78 (dm, 1H, J=48.7 Hz), 7.03–7.06 (m, 1H), 7.14–7.16 (m, 1H), 7.34–7.41 (m, 2H), 8.18–8.22 (m, 1H), 9.01 (s, 2H)

MS(m/z): 598 (M$^+$)

This compound melted and exhibited an antiferroelectric liquid crystal phase at a temperature of 82° C. and changed to an isotropic phase at a temperature of 95° C. This compound was injected into a liquid crystal cell, and then measured for threshold voltage at a temperature of 90° C. As a result, the threshold voltage was as very low as ±7 V.

Example 6

Synthesis of 5-(4-((R)-3-fluorodecyloxy)phenyl)-2-(4-((S)- 2,6-dimethylheptanoyloxy)phenyl)-1,3-pyrimidine The procedure of Example 1 was followed except that (S)-2-fluorooctyl tosylate was replaced by (R)-3-fluorodecyl mesylate in the step (1). Thus, the desired compound was obtained.

$^1$H-NMR(CDCl$_3$) δ ppm: 0.89–0.91 (m, 9H), 1.21–1.28 (m, 2H), 1.32–1.38 (m, 8H), 1.41–1.49 (m, 4H), 1.55–1.60 (m, 1H), 1.78–1.86 (m, 3H), 2.08 (m, 1H), 2.12 (m, 1H), 2.71–2.73 (m, 1H), 4.71–4.81 (m, 1H), 7.06 (d, 2H, J=8.9 Hz), 7.22 (d, 2H, J=8.9 Hz), 7.56 (d, 2H, J=8.8 Hz), 8.51 (d, 2H, J=9.0 Hz), 8.97 (s, 2H)

MS(m/z): 562 (M$^+$)

This compound melted and exhibited an antiferroelectric liquid crystal phase at a temperature of 132.2° C., exhibited a ferroelectric liquid crystal phase at a temperature of 151.7° C. and changed to an isotropic phase at a temperature of 152.6° C. This compound was injected into a liquid crystal cell, and then measured for tilt angle and threshold voltage. The results were 40 degrees and 35 V, respectively. This compound has a threshold voltage which is higher than the compound having 2-fluoroalkyl group incorporated therein but lower than the compound set forth in Comparative Example 1 and a tilt angle as very wide as 40 degrees. The optimum tilt angle of an antiferroelectric liquid crystal is 45 degrees. Known antiferroelectric liquid crystals have a tilt angle as low as about 30 degrees. The compound obtained above has a tilt angle of 40 degrees, which is close to the optimum value. Thus, it was found that the compound obtained above has very excellent properties.

Example 7

Synthesis of 5-(4-((R)-3-fluorooctyloxy)phenyl)-2-(4-((S)-2,6-dimethylheptanoyloxy)phenyl)-1,3-pyrimidine The procedure of Example 6 was followed except that (R)-3-fluorodecyl mesylate was replaced by (R)-3-fluorooctyl mesylate. Thus, the desired compound was obtained.

$^1$H-NMR(CDCl$_3$) δ ppm: 0.89–0.91 (m, 9H), 1.21–1.28 (m, 2H), 1.32–1.38 (m, 8H), 1.41–1.49 (m, 4H), 1.55–1.60 (m, 1H), 1.78–1.86 (m, 3H), 2.08 (m, 1H), 2.12 (m, 1H), 2.71–2.73 (m, 1H), 4.15–4.21 (m, 2H), 4.78 (dm, 1H, J=48.7 Hz), 7.06 (d, 2H, J=8.9 Hz), 7.22 (d, 2H, J=8.9 Hz), 7.56 (d, 2H, J=8.8 Hz), 8.51 (d, 2H, J=9.0 Hz), 8.97 (s, 2H)

MS(m/z): 534 (M$^+$)

This compound melted and exhibited an antiferroelectric liquid crystal phase at a temperature of 116.3° C. and changed to an isotropic phase at a temperature of 146.9° C.

Example 8

Synthesis of 5-((S)-2-fluorodecyloxy)-2-(4-((S)-2-methylheptanoyloxy)phenyl)-1,3-pyrimidine (1) Synthesis of 5-((S)-2-fluorodecyloxy)-2-(4-benzyloxyphenyl)-1,3-pyrimidine Into a reaction flask were charged 0.7 g of 5-hydroxy-2-(4-benzyloxyphenyl)-1,3-pyrimidine, 0.94 g of (S)-2-fluorodecyl tosylate, 10 ml of DMF and 0.52 g of potassium carbonate in a stream of nitrogen. The mixture was then stirred at a temperature of 80° C. in a stream of nitrogen for 20 hours. The reaction product was allowed to cool, poured into ice water, and then extracted with chloroform. The extract was then subjected to distillation of chloroform to obtain 1.8 g of a crude reaction product. The crude reaction product was then purified through silica gel column chromatography (toluene/ethyl acetate=10/1) to obtain 1.1 g of the desired compound (yield: 96.3%).

(2) Synthesis of 5-((S)-2-fluorodecyloxy)-2-(4-hydroxyphenyl)-1,3-pyrimidine

Into a reaction flask were charged 1.1 g of 5-((S)-2-fluorodecyloxy)-2-(4-benzyloxyphenyl)-1,3-pyrimidine, 50 ml of THF, 20 ml of methanol and 0.22 g of palladium-carbon (10% in a stream of nitrogen). The atmosphere in the flask was then replaced by hydrogen. The mixture was then subjected to hydrogenation at ordinary pressure.

After the termination of the reaction, palladium-carbon was removed by filtration. The solvent was then distilled off the filtrate to obtain 0.92 g of a crude reaction product. The crude reaction product was then purified through silica gel column chromatography (toluene/ethyl acetate=3/1) to obtain 0.6 g of the desired compound (yield: 84.4%).

(3) Synthesis of 5-((S)-2-fluorodecyloxy)-2-(4-((S)-2-methylheptanoyloxy)phenyl)-1,3-pyrimidine Into a reaction flask were charged 0.6 g of 5-((S)-2-fluorodecyloxy)-2-(4-hydroxyphenyl)-1,3-pyrimidine, 30 ml of methylene chloride, 0.51 g of DCC and a small amount of DMAP. The mixture was stirred at room temperature overnight. The insoluble matter was removed by filtration. The solvent was distilled off the filtrate to obtain a crude reaction product which was then purified through silica gel column chromatography (toluene/ethyl acetate=3/1) to obtain 0.42 g of the desired compound (yield: 53.8%).

$^1$H-NMR(CDCl$_3$) δ ppm: 0.89–0.93 (m, 6H), 1.32–1.45 (m, 17H), 1.55–1.60 (m, 1H), 1.78–1.84 (m, 3H), 2.73–2.78 (m, 1H), 4.18–4.20 (m, 1H), 4.24–4.25 (m, 1H), 4.87 (dm, 1H, J=48.6 Hz), 7.17–7.21 (m, 1H), 8.15–8.20 (m, 2H), 8.48 (s, 2H)

MS(m/z): 463 (M$^+$+H)

This compound melted and changed to an isotropic phase at a temperature of 70° C. and then exhibited an antiferroelectric liquid crystal phase when cooled. The phase transition temperature from an antiferroelectric liquid crystal phase to an isotropic phase was 42° C.

Example 9

Synthesis of 5-((S)-2-fluorooctyloxy)-2-(3-fluoro-4-((S)-2-methylheptanoyloxy)phenyl)-1,3-pyrimidine The procedure of Example 8 was followed except that 5-hydroxy-2-(4-benzyloxyphenyl)-1,3-pyrimidine was replaced by 5-hydroxy-2-(3-fluoro-4-benzyloxyphenyl) pyrimidine and (S)-2-fluorodecyl tosylate was replaced by (S)-2-fluorooctyl tosylate. Thus, the desired compound was obtained.

$^1$H-NMR(CDCl$_3$) δ ppm: 0.87–0.93 (m, 6H), 1.29–1.45 (m, 21H), 1.80–1.87 (m, 4H), 2.68–2.73 (m, 1H), 4.18–4.29 (m, 1H), 4.23–4.24 (m, 1H), 4.87 (dm, 1H, J=48.5 Hz), 7.17 (d, 2H, J=8.9 Hz), 8.38 (d, 2H, J=8.9 Hz), 8.47 (s, 2H)

MS(m/z): 473 (M$^+$+H)

This compound melted and changed to an isotropic phase at a temperature of 39.6° C. and then monotropically exhibited an antiferroelectric liquid crystal phase when cooled. The phase transition temperature from the antiferroelectric liquid crystal phase to the isotropic phase was 29° C.

Example 10

Synthesis of 5-(4-((R)-1-trifluoromethylheptyloxy carbonyl)phenyl)-2-(3-fluoro-4-((S)-2-fluorooctyloxy)phenyl)-1,3-pyrimidine (1) Synthesis of 5-(4-methoxycarbonylphenyl)-2-(3-fluoro-4-((S)-2-fluorooctyloxy)phenyl)-1,3-pyrimidine Into a reaction flask were charged 0.71 g of (S)-2-fluorooctyl tosylate, 0.7 g of 5-(4-methoxycarbonylphenyl)-2-(3-fluoro-4-hydroxyphenyl)-1,3-pyrimidine, 0.60 g of potassium carbonate and 30 ml of dimethylformamide (DMF) in a stream of nitrogen. The mixture was then stirred at a temperature of 80° C. in a stream of nitrogen for 2 hours.

The reaction product was allowed to cool, poured into ice water, and then extracted with ethyl acetate. The extract was washed with saturated brine, dried, and then subjected to distillation of solvent to obtain a crude reaction product. The crude reaction product was then purified through silica gel column chromatography (benzene/ethyl acetate) to obtain 0.64 g of the desired compound (yield: 65.3%).

(2) Synthesis of 5-(4-carboxyphenyl)-2-(3-fluoro-4-((S)-2-fluorooctyloxy)phenyl)-1,3-pyrimidine Into a reaction flask were charged 0.64 g of 5-(4-methoxycarbonylphenyl)-2-(3-fluoro-4-((S)-2-fluorooctyloxy)phenyl-1,3-pyrimidine, 0.12 g of potassium hydroxide, 1 ml of water and 40 ml of ethanol. The reaction mixture was then allowed to undergo reaction at a temperature of from 80° C. to 85° C. for 4 hours. The reaction system was then allowed to cool. The reaction product was poured into water, acidified with hydrochloric acid, and then extracted with ethyl acetate. The resulting organic phase was washed with saturated brine under heating, and then concentrated to obtain a crude reaction product. The crude reaction product was then purified through silica gel column chromatography (benzene/ethyl acetate) to obtain 0.59 g of the desired compound (yield: 95.1%).

(3) Synthesis of 5-(4-((R)-1-trifluoromethylheptyl oxycarbonyl)phenyl)-2-(3-fluoro-4-((S)-2-fluorooctyloxy) phenyl)-1,3-pyrimidine Into a reaction flask were charged 0.59 g of 5-(4-carboxyphenyl)-2-(3-fluoro-4-((S)-2-fluorooctyloxy) phenyl)-carboxyphenyl)-1,3-pyrimidine, 0.40 g of (R)-1,1,1-trifluoro-2-octanol, 0.64 g of DCC, 87 mg of DMAP, 30 ml of THF and 15 ml of methylene chloride. The mixture was stirred at room temperature for 2 hours. The resulting salt was withdrawn by filtration, and then concentrated to obtain a crude reaction product which was then purified through silica gel column chromatography to obtain 0.24 g of the desired compound (yield: 29.6%).

$^1$H-NMR(CDCl$_3$) δ ppm: 0.87 (t, 3H, J=6.9 Hz), 0.90 (t, 3H, J=7.0 Hz), 1.22–1.95 (m, 20H), 4.16–4.33 (m, 2H), 4.90 (dm, 1H, J=48.9 Hz), 5.52–5.63 (m, 1H), 7.09 (t, 1H, J=8.4 Hz), 7.74 (d, 2H, J=8.7 Hz), 7.55 (d, 2H, J=8.3 Hz), 8.20–8.28 (m, 2H), 9.02 (s, 2H)

MS(m/z): 606 (M$^+$)

This compound melted and changed to an isotropic phase at a temperature of 113.8° C. Even when cooled, this compound exhibited no liquid crystal phase. However, when this compound was added to the compound set forth in Comparative Example 1 in an amount of 9.98% by weight, an antiferroelectric liquid crystal composition (Tc=118.5° C.) was obtained. This composition was injected into a liquid crystal cell, and then measured for threshold voltage at a temperature of (Tc-5° C.). The results were 30.4 V. The compound of Comparative Example 1 has a threshold voltage of 44 V at a temperature of (Tc-5° C.). Thus, it can be seen that the incorporation of the compound of Example 10 provides an improvement in threshold voltage, making it possible to obtain an antiferroelectric liquid crystal composition having better properties.

Example 11

Synthesis of 5-(4-(S)-1-trifluoromethylheptyloxy carbonyl)phenyl-2-(4-((S)-2-fluorooctyloxy)phenyl)-1,3-pyrimidine The procedure of Example 10 was followed except that 5-(4-methoxycarbonylphenyl)-2-(3-fluoro-4-hydroxyphenyl)-1,3-pyrimidine was replaced by 5-(4-methoxycarbonylphenyl)-2-(4-hydroxyphenyl)-1,3-pyrimidine and (R)-1,1,1-trifluoro-2-octanol was replaced by (S)-1,1,1-trifluoro-2-octanol. Thus, the desired compound was obtained.

$^1$H-NMR(CDCl$_3$) δ ppm: 0.87 (t, 3H, J=7.1 Hz), 0.90 (t, 3H, J=7.0 Hz), 1.22–1.62 (m, 16H), 1.65–1.97 (m, 4H), 4.09–4.24 (m, 2H), 4.87 (dm, 1H, J=48.9 Hz), 5.53–5.63 (m, 1H), 7.05 (d, 2H, J=9.0 Hz), 7.73 (d, 2H, J=8.7 Hz), 8.23 (d, 2H, J=8.7 Hz), 8.47 (d, 2H, J=9.0 Hz), 9.01 (s, 2H)

MS(m/z): 588 (M$^+$)

This compound melted and changed to an isotropic phase at a temperature of 100.5° C. and then monotropically exhibited a smectic A phase (SmA phase) and antiferroelectric liquid crystal phase when cooled. The phase transition temperature from the antiferroelectric liquid crystal phase to the SmA phase was 83.5° C. The phase transition temperature from the SmA phase to the isotropic phase was 91° C.

Example 12

Synthesis of 5-(3-fluoro-4-((S)-2-fluorooctyloxy) phenyl)-2-(4-((R)-1-trifluoromethylheptyloxycarbonyl)phenyl)-1,3-pyrimidine The procedure of Example 10 was followed except that 5-(4-methoxycarbonylphenyl)-2-(3-fluoro-4-hydroxyphenyl)-1,3-pyrimidine was replaced by 5-(3-fluoro-4-hydroxyphenyl)-2-(4-methoxycarbonylphenyl)-1,3-pyrimidine. Thus, the desired compound was obtained.

$^1$H-NMR(CDCl$_3$) δ ppm: 0.87 (t, 3H, J=7.0 Hz), 0.90 (t, 3H, J=6.9 Hz), 1.22–1.60 (m, 16H), 1.65–1.97 (m, 4H), 4.15–4.28 (m, 2H), 4.89 (dm, 1H, J=48.8 Hz), 5.53–5.63 (m, 1H), 7.15 (t, 1H, J=8.5 Hz), 7.34–7.52 (m, 2H), 8.21 (d, 2H, J=8.7 Hz), 8.60 (d, 2H, J=8.8 Hz), 9.00 (s, 2H)

MS(m/z): 606 (M$^+$)

This compound melted and changed to an isotropic phase at a temperature of 100.1° C. Even when cooled rapidly, this compound exhibited no liquid crystal phase. However, when this compound was added to the compound set forth in Comparative Example 1 in an amount of 10.0% by weight, an antiferroelectric liquid crystal composition (Tc=115.7° C.) was obtained. This composition was injected into a liquid crystal cell, and then measured for threshold voltage at a temperature of (Tc-5° C.). As a result, the threshold voltage was 24.8 V. The compound of Comparative Example 1 h as a threshold voltage of 44 V at a temperature of (Tc-5° C.). Thus, it can be seen that the incorporation of the compound of Example 12 provides an improvement in threshold voltage, making it possible to obtain an antiferroelectric liquid crystal composition having better properties.

Example 13

Synthesis of 5-(4-((S)-2-fluorodecyloxy) phenyl)-2-(4-((R)-1-trifluoromethylheptyloxycarbonyl)phenyl)-1,3-pyrimidine The procedure of Example 10 was followed except that 5-(4-methoxycarbonylphenyl)-2-(3-fluoro-4-hydroxyphenyl)-1,3-pyrimidine was replaced by 5-(4-hydroxyphenyl)-2-(4-methoxycarbonylphenyl)-1,3-pyrimidine and (S)-2-fluorooctyl tosylate was replaced by (S)-2-fluorodecyl mesylate. Thus, the desired compound was obtained.

$^1$H-NMR(CDCl$_3$) δ ppm: 0.87 (t, 3H, J=7.1 Hz), 0.89 (t, 3H, J=7.0 Hz), 1.20–1.95 (m, 24H), 4.07–4.20 (m, 2H), 4.87 (dm, 1H, J=48.9 Hz), 5.59 (m, 1H), 7.09 (d, 2H, J=8.8 Hz), 7.59 (d, 2H, J=8.8 Hz), 8.20 (d, 2H, J=8.7 Hz), 8.59 (d, 2H, J=8.7 Hz), 9.03 (s, 2H)

MS(m/z): 616 (M$^+$)

This compound melted and changed at a temperature of 117.8° C. Even when cooled rapidly, this compound exhibited no liquid crystal phase. However, when this compound was added to the compound set forth in Comparative Example 1 in an amount of 9.8% by weight, an antiferroelectric liquid crystal composition (Tc=122.0° C.) was obtained. This composition was injected into a liquid crystal cell, and then measured for threshold voltage at a temperature of (Tc-5° C.). As a result, the threshold voltage was 25.6 V. The compound of Comparative Example 1 has a threshold voltage of 44 V at a temperature of (Tc-5° C.). Thus, it can be seen that the incorporation of the compound of Example 13 provides an improvement in threshold voltage, making it possible to obtain an antiferroelectric liquid crystal composition having better properties.

Example 14

Synthesis of 5-(4-((S)-2-fluorooctyloxy) phenyl)-2-(4-((R)-1-trifluoromethylheptyloxycarbonyl)phenyl)-1,3-pyrimidine The procedure of Example 10 was followed except that 5-(4-methoxycarbonylphenyl)-2-(3-fluoro-4-hydroxyphenyl)-1,3-pyrimidine was replaced by 5-(4-hydroxyphenyl)-2-(4-methoxycarbonylphenyl)-1,3-pyrimidine. Thus, the desired compound was obtained.

$^1$H-NMR(CDCl$_3$) δ ppm: 0.87 (t, 3H, J=7.1 Hz), 0.91 (t, 3H, J=7.1 Hz), 1.20–1.95 (m, 20H), 4.07–4.22 (m, 2H), 4.87 (dm, 1H, J=48.9 Hz), 5.59 (m, 1H), 7.09 (d, 2H, J=8.8 Hz), 7.59 (d, 2H, J=8.9 Hz), 8.21 (d, 2H, J=8.8 Hz), 8.59 (d, 2H, J=8.7 Hz), 9.03 (s, 2H)

MS(m/z): 588 (M$^+$)

This compound melted and changed to an isotropic phase at a temperature of 110.5° C. Even when rapidly cooled, this compound exhibited no liquid crystal phase. However, when this compound was added to the compound set forth in Comparative Example 1 in an amount of 9.8% by weight, an antiferroelectric liquid crystal composition (Tc=119.4° C.) was obtained. This composition was injected into a liquid crystal cell, and then measured for threshold voltage at a temperature of (Tc-5° C.). As a result, the threshold voltage was 31.6 V. The compound of Comparative Example 1 has a threshold voltage of 44 V at a temperature of (Tc- 5° C.). Thus, it can be seen that the incorporation of the compound of Example 14 provides an improvement in threshold voltage, making it possible to obtain an antiferroelectric liquid crystal composition having better properties.

Example 15

Synthesis of 5-(4-((R)-1-trifluoromethylheptyloxy carbonyl)phenyl-2-(4-((S)-2,6-dimethylheptanoyloxy)phenyl)-1,3-pyrimidine (1) Synthesis of 5-(4-((R)-1-trifluoromethylheptyl oxycarbonyl)phenyl-2-(4-benzyloxyphenyl)-1,3-pyrimidine 0.69 g of 5-(4-carboxyphenyl)-2-(4-benzyloxyphenyl)-1,3-pyrimidine, 0.57 g of (R)-1,1,1-trifluorooctanol, 0.89 g of DCC, 0.22 g of DMAP and 60 ml of DMF were stirred at room temperature in a stream of nitrogen overnight, and then reacted at a temperature of 60° C. for 1 day. The unreacted carboxylic acid derivatives and the resulting salts were withdrawn by filtration, poured into water, extracted with ethyl acetate, and then concentrated to obtain 0.7 g of a crude reaction product. The crude reaction product was then purified through silica gel column chromatography (benzene-ethyl acetate system) to obtain 0.32 g of the desired compound (yield: 32.3%).

(2) Synthesis of 5-(4-((R)-1-trifluoromethylheptyl oxycarbonyl)phenyl-2-(4-hydroxyphenyl)-1,3-pyrimidine Into a reaction flask were charged 0.50 g of 5-(4-((R)-1-trifluoromethylheptyloxycarbonyl)phenyl-2-(4-benzyloxyphenyl)-1,3-pyrimidine, 0.4 g of 10% palladium-carbon (Pd—C), 0.4 g of sodium acetate, 20 ml of THF and 5 ml of methanol in a stream of nitrogen. The atmosphere in the reaction flask was then replaced by hydrogen. The reaction mixture was then stirred at room temperature for 6 hours. The catalyst was then removed by filtration. The filtrate was then concentrated to obtain a crude reaction product. The crude reaction product was purified through silica gel column chromatography, and then recrystallized from hexane to obtain 0.33 g of the desired compound (yield: 78.6%).

(3) Synthesis of 5-($^4$-((R)-1-trifluoromethylheptyl oxycarbonyl)phenyl)-2-(4-((S)-2,6-dimethylheptanoyloxy)phenyl)-1,3-pyrimidine Into a reaction flask were charged 0.20 g of 5-(4-((R)-1-trifluoromethylheptyloxycarbonyl)phenyl)-2-(4-hydroxyphenyl)-1,3-pyrimidine, 0.091 g of (S)-2,6-dimethylheptanoic acid, 0.18 g of DCC, 0.044 g of DMAP, 20 ml of THF and 10 ml of methylene chloride. The mixture was stirred at room temperature for 2 hours. The resulting salt was withdrawn by filtration, concentrated, purified through silica gel column chromatography (benzene-ethyl acetate), and then fractionated by medium pressure liquid chromatography to obtain 0.2 g of the desired compound (yield: 76.9%). [α] D25=−26.8° (C=0.82, CH$_2$Cl$_2$)

$^1$H-NMR(CDCl$_3$) δ ppm: 0.85–0.92 (m, 9H), 1.20–1.97 (m, 20H), 2.73 (m, 1H), 5.58 (m, 1H), 7.24 (d, 2H, J=8.9 Hz), 7.75 (d, 2H, J=8.6 Hz), 8.24 (d, 2H, J=8.7 Hz), 8.55 (d, 2H, J=9.0 Hz), 9.05 (s, 2H)

MS(m/z): 598 (M$^+$)

This compound melted and changed to an isotropic phase at a temperature of 65.1° C. When rapidly cooled, this compound exhibited an unidentified liquid crystal phase at a temperature of 25.5° C. When this compound was added to the compound set forth in Comparative Example 1 in an amount of 10.0% by weight, an antiferroelectric liquid crystal composition (Tc=106.5° C.) was obtained. This composition was injected into a liquid crystal cell, and then measured for threshold voltage at a temperature of (Tc-5° C.). As a result, the threshold voltage was 37.2 V. The compound of Comparative Example 1 has a threshold voltage of 44 V at a temperature of (Tc-5° C.). Thus, it can be seen that the incorporation of the compound of Example 15 provides an improvement in threshold voltage, making it possible to obtain an antiferroelectric liquid crystal composition having better properties.

Example 16

Synthesis of 5-(3-fluoro-4-((S)-2-fluorooctyloxy) phenyl-2-(3-fluoro-4-((S)-2-fluorooctyloxy)phenyl)-1,3-pyrimidine The procedure of Example 10 was followed except that 5-(4-methoxycarbonylphenyl)-2-(3-fluoro-4-hydroxyphenyl)-1,3-pyrimidine was replaced by 5-(3-fluoro-4-hydroxyphenyl)-2-(3-fluoro-4-hydroxyphenyl)-1,3-pyrimidine in the step (1). Thus, the desired compound was obtained.

$^1$H-NMR(CDCl$_3$) δ ppm: 0.90 (t, 6H, J=6.9 Hz), 1.20–1.92 (m, 22H), 4.07–4.32 (m, 4H), 4.89 (dm, 2H, J=48.7 Hz), 7.05–7.15 (m, 2H), 7.31–7.38 (m, 2H), 8.21–8.25 (m, 2H), 8.91 (s, 2H)

MS(m/z): 560 (M⁺)

This compound melted and exhibited a ferroelectric liquid crystal phase (SmC* phase) at a temperature of 86.1° C., changed to a SmA phase at a temperature of 157.1° C., and then became an isotropic phase at a temperature of 178° C. When this compound was added to the compound set forth in Comparative Example 1 in an amount of 9.95% by weight, an antiferroelectric liquid crystal composition (Tc= 125.1° C.) was obtained. This composition was injected into a liquid crystal cell, and then measured for threshold voltage at a temperature of (Tc-5° C.). As a result, the threshold voltage was 19.2 V. The compound of Comparative Example 1 has a threshold voltage of 44 V at a temperature of (Tc-5° C.). Thus, it can be seen that the incorporation of the compound of Example 16 provides a remarkable improvement in threshold voltage, making it possible to obtain an antiferroelectric liquid crystal composition having better properties.

Example 17

Synthesis of 5-(4-((R)-2-fluoroheptanoyloxy) phenyl-2-(4-((S)-2-methylheptanoyloxy)phenyl)-1,3-pyrimidine The procedure of Example 1 was followed except that (S)-2-fluorooctyl tosylate was replaced by (R)-2-fluoroheptanoic acid in the step (1) and the esterification was effected in the same manner as in the step (3) but (S)-2,6-dimethylheptanoic acid was replaced by 2-methylheptanoic acid. Thus, the desired compound was obtained.

¹H-NMR(CDCl₃) δ ppm: 0.91 (t, 3H, J=7.1 Hz), 0.94 (t, 3H, J=7.0 Hz), 1.20–1.50 (m, 10H), 1.32 (d, 3H, J=7 Hz), 1.53–1.65 (m, 3H), 1.80–1.90 (m, 1H), 2.02–2.18 (m, 2H), 2.72 (m, 1H), 5.18 (dt, 1H, J=48.7 Hz, J=5.9 Hz), 7.35 (d, 2H, J=8.8 Hz), 7.30 (d, 2H, J=8.7 Hz), 7.66 (d, 2H, J=8.6 Hz), 8.53 (d, 2H, J=8.8 Hz), 8.99 (s, 2H)

MS(m/z): 520 (M⁺)

This compound melted and exhibited a ferroelectric liquid crystal phase (SmC* phase) at a temperature of 138.7° C., and then became an isotropic phase at a temperature of 147.3° C. When this compound was added to the compound set forth in Comparative Example 1 in an amount of 9.95% by weight, an antiferroelectric liquid crystal composition (Tc=125.1° C.) was obtained. This composition was injected into a liquid crystal cell, and then measured for threshold voltage at a temperature of (Tc-5° C.). As a result, the threshold voltage was 40.4 V. The compound of Comparative Example 1 has a threshold voltage of 44 V at a temperature of (Tc-5° C.). Thus, it can be seen that the incorporation of the compound of Example 17 provides an improvement in threshold voltage, making it possible to obtain an antiferroelectric liquid crystal composition having better properties.

Example 18

An antiferroelectric liquid crystal composition can be obtained by mixing the compounds of the present invention and a known compound which exhibits an antiferroelectric liquid crystal phase or its composition.

Compound of Example 1 16.79% by weight
Compound of Example 5 15.99% by weight
Compound of Example 7 17.88% by weight
Compound of Example 8 20.06% by weight
Compound of Example 9 17.40% by weight
TFMHPOBC 11.88% by weight TFMHPOBC (4'-octyloxybiphenyl-4-carboxylic acid-4-(1-trifluoromethylheptyloxycarbonyl)phenyl) is a known antiferroelectric liquid crystal having the following structural formula:

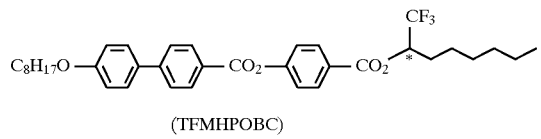

(TFMHPOBC)

This liquid crystal composition melted and exhibited an antiferroelectric liquid crystal phase at a temperature of 20° C., changed to a smectic A phase at a temperature of 63° C., and then changed to an isotropic phase at a temperature of 70° C. This liquid crystal composition was then injected into a liquid crystal cell. The specimen was then observed under a polarizing microscope while being placed under the application of a triangular wave voltage. As a result, a double hysteresis inherent to antiferroelectric liquid crystal was observed. Thus, an antiferroelectric liquid crystal composition was obtained.

As mentioned above, the compound of the present invention has a good miscibility with a known compound which exhibits an antiferroelectric liquid crystal phase or its composition and thus can easily form an antiferroelectric liquid crystal composition.

Example 19

An antiferroelectric liquid crystal composition was composed of the compounds set forth in Table 5.

TABLE 5

| Compound | % by weight |
|---|---|
| C₁₀H₂₁—⟨phenyl⟩—⟨pyrimidine⟩—⟨phenyl⟩—O—C(=O)—*CH(CH₃)—(CH₂)₃CH(CH₃)₂ | 29.93 |
| C₁₀H₂₁OC(O)O—⟨phenyl⟩—⟨pyrimidine⟩—⟨phenyl⟩—O—C(=O)—*CH(CH₃)—(CH₂)₃CH(CH₃)₂ | 29.57 |

TABLE 5-continued

| Compound | % by weight |
|---|---|
|  | 9.57 |
|  | 30.93 |

This antiferroelectric liquid crystal composition changed to an antiferroelectric liquid crystal phase directly from an isotropic phase. The phase transition temperature was 92.3° C. This liquid crystal composition was injected into a liquid crystal cell, and then measured for threshold voltage at a temperature of 72.3° C. (Tc-20° C.). As a result, the threshold voltage was 35.6 V.

Comparative Example 2 below will give the results of measurement of an antiferroelectric liquid crystal composition composed in the same manner as above except that the compound of the present invention was replaced by a compound free of fluorine-substituted alkyl chain but having a straight-chain alkyl chain incorporated therein. The composition of the present example exhibited a threshold voltage 20 V lower than the composition of Comparative Example 2, which is a remarkable improvement in the threshold voltage.

Figure 2:
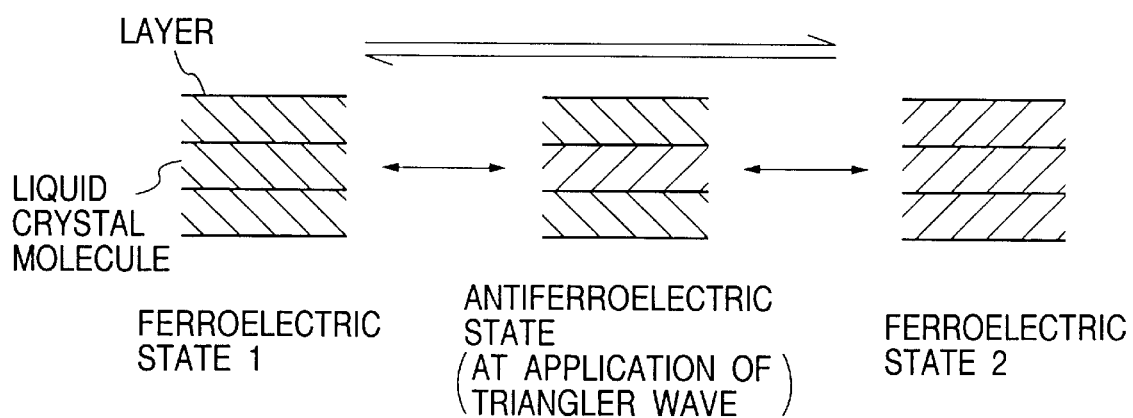
FIG. 2 is a typical diagram of response of a liquid crystal molecule under the application of a rectangular or triangular wave.

On the other hand, it is known that when a rectangular wave alternating electric field is applied to an antiferroelectric liquid crystal, the antiferroelectric liquid crystal is observed to give a response between ferroelectric states skipping an antiferroelectric state as shown in FIG. 2. The antiferroelectric liquid crystal composition was then measured for switching time between ferroelectric states under the application of a ±50 V rectangular wave. As a result, the switching time was as very fast as 3.3 μs. When the results are compared with that of Comparative Example 2, it can be seen that the antiferroelectric liquid crystal composition of the present example shows an improved response attributed to the viscosity drop.

Comparative Example 2

An antiferroelectric liquid crystal composition was composed in the same manner as in Example 19 except that the compound of the present invention was replaced by a compound free of fluorine-substituted alkyl chain but having a straight-chain alkyl chain incorporated therein.

TABLE 6

| Compound | % by weight |
|---|---|
| 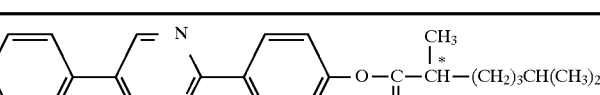 | 29.41 |
| 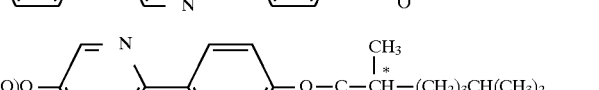 | 29.83 |
| 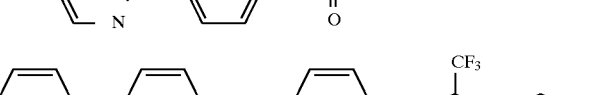 | 9.77 |
| 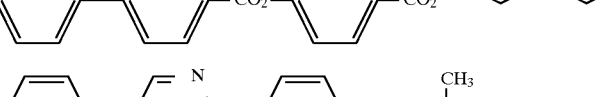 | 30.99 |

This liquid crystal composition changed from an isotropic phase to a smectic A phase at a temperature of 89.3° C., and then changed to an antiferroelectric liquid crystal phase at a temperature of 86.9° C. When measured at a temperature of 66.9° C. (Tc-20° C.), this antiferroelectric liquid crystal composition exhibited a threshold voltage of 56.9 V, which is higher than that of Example 19. Thus, it can be seen that the incorporation of the compound of the present invention can provide a drastic improvement in threshold voltage as shown in Example 19. When measured at the same temperature in the same manner as in Example 19, this antiferroelectric liquid crystal composition also exhibited a switching time of 7.2 μs between ferroelectric states, which is not less than double that of Example 19. This shows that the compound of the present invention of Example 19 provides a viscosity drop.

Example 20

An antiferroelectric liquid crystal composition was formed in the same manner as in Example 19 except that a compound of the general formula (I) wherein q is 2 was used.

TABLE 7

| Compound | % by weight |
|---|---|
|  | 30.11 |
| 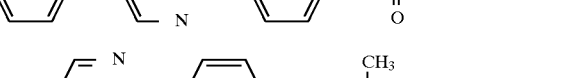 | 29.90 |
| 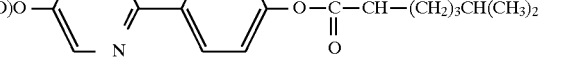 | 10.15 |
| 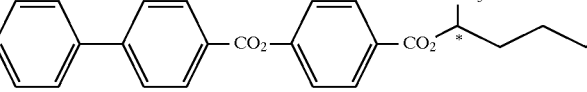 | 29.84 |

This antiferroelectric liquid crystal composition changed to an antiferroelectric liquid crystal phase directly from an isotropic phase. The phase transition temperature was 87.9° C. This liquid crystal composition was injected into a liquid crystal cell, and then measured for threshold voltage at a temperature of 57.9° C. (Tc-20° C.). As a result, the threshold voltage was 46.4 V.

The compound of the general formula (I) wherein n is 2 can exert a smaller effect of reducing the threshold voltage than the compound of the general formula (I) wherein q is 1. The compound of the general formula (I) wherein q is 2 can still provide an improvement in threshold voltage as compared with Comparative Example 2.

On the other hand, when measured at the same temperature as in Example 19, this antiferroelectric liquid crystal composition exhibited a switching time of 3.75 μs between ferroelectric states, which is as fast as Example 19. This shows that the compound of the present example, too, has a low viscosity.

The optically active compound of the present invention has a good miscibility with many known antiferroelectric liquid crystal compounds and thus can provide a liquid crystal material having improved temperature characteristics. Further, a liquid crystal composition containing an optically active compound of the present invention can be incorporated in electro-optical elements employing an antiferroelectric liquid crystal.

While the invention has been described in detail and with reference to specific embodiments thereof, it will be apparent to one skilled in the art that various changes and modifications can be made therein without departing from the spirit and scope thereof.

What is claimed is:

1. An optically active compound, represented by the following general formula (I):

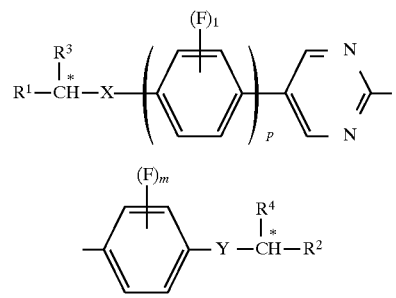

wherein $R^1$ represents an alkyl group of 5 to 10 carbon atoms; $R^2$ represents an alkyl group of 3 to 10 carbon atoms or an alkyl group of 4 to 12 carbon atoms having a $C_{1-3}$ branched group; $R^3$ represents a fluorine atom, a methyl group or a trifluoromethyl group; $R^4$ represents a methyl group, a fluorine atom or a trifluoromethyl group; 1, m and p each represent 0 or 1; X represents $-(CH_2)_q-O-$, $-OCO-$ or $-CO_2-$; Y represents $-OCO-$, $-CO_2-$ or $-O-(CH_2)_n-$ in which n and q each represent 1 or 2, with the proviso that in the case where p is 1, $R^3$ represents a fluorine atom if X is $-(CH_2)_q-O-$, and the further proviso that independent of the situation where p is 1, $R^4$ represents a fluorine atom if Y is $-O-(CH_2)_n-$, or in the case where p is 0, neither $R^3$ nor $R^4$ is a fluorine atom if X is $-(CH_2)_q-O-$ or $-CO_2-$ and Y is $-OCO-$ or $-O-(CH_2)_n-$; and C* represents an asymmetric carbon atom, with the further proviso that in the case where p is 1, X is —OCO— and Y is —CO$_2$—, one of R$^3$ and R$^4$ does not represent a fluorine atom.

2. An antiferroelectric liquid crystal composition having a reduced threshold voltage containing at least one optically active compound represented by the following general formula (I):

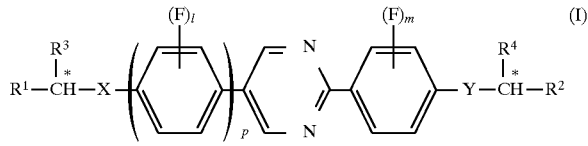

wherein R$^1$ represents an alkyl group of 5 to 10 carbon atoms; R$^2$ represents an alkyl group of 3 to 10 carbon atoms or an alkyl group of 4 to 12 carbon atoms having a C$_{1-3}$ branched group; R$^3$ represents a fluorine atom, a methyl group or a trifluoromethyl group; R$^4$ represents a methyl group, a fluorine atom or a trifluoromethyl group; l, m and p each represent 0 or 1; X represents —(CH$_2$)$_q$—O—, —OCO— or —CO$_2$—; Y represents —OCO—, —CO$_2$— or —O—(CH$_2$)$_n$— in which n and q each represent 1 or 2, with the proviso that in the case where p is 1, R$^3$ represents a fluorine atom, if X is —(CH$_2$)$_q$—O—, and R$^4$ represents a fluorine atom, if Y is —O—(CH$_2$)$_n$—, or in the case where p is 0, neither R$^3$ nor R$^4$ is a fluorine atom, if X is —(CH$_2$)$_q$—O— or —CO$_2$— and Y is —OCO— or —O—(CH$_2$)$_n$—; and C* represents an asymmetric carbon atom.

3. A process for the reduction of the threshold voltage of an antiferroelectric liquid crystal composition, which comprises incorporating at least one optically active compound represented by the following general formula (I) into an antiferroelectric liquid crystal composition to reduce the threshold voltage of the composition:

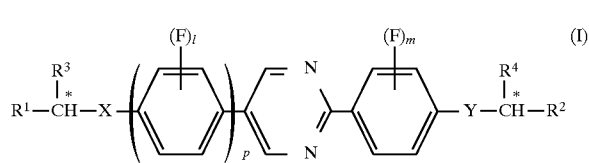

wherein R$^1$ represents an alkyl group of 5 to 10 carbon atoms; R$^2$ represents an alkyl group of 3 to 10 carbon atoms or an alkyl group of 4 to 12 carbon atoms having a C$_{1-3}$ branched group; R$^3$ represents a fluorine atom, a methyl group or a trifluoromethyl group; R$^4$ represents a methyl group, a fluorine atom or a trifluoromethyl group; l, m and p each represent 0 or 1; X represents —(CH$_2$)$_q$—O—, —OCO— or —CO$_2$—; Y represents —OCO—, —CO$_2$— or —O—(CH$_2$)$_n$— in which n and q each represent 1 or 2, with the proviso that in the case where p is 1, R$^3$ represents a fluorine atom, if X is —(CH$_2$)$_q$—O—, and R$^4$ represents a fluorine atom, if Y is —O—(CH$_2$)$_n$—, or in the case where p is 0, neither R$^3$ nor R$^4$ is a fluorine atom, if X is —(CH$_2$)$_q$—O— or —CO$_2$— and Y is —OCO— or —O—(CH$_2$)$_n$—; and C* represents an asymmetric carbon atom.

* * * * *